(12) United States Patent  (10) Patent No.: US 8,739,795 B2
Kanowitz  (45) Date of Patent: *Jun. 3, 2014

(54) COMPLETE AIRWAY STABILIZATION SYSTEM

(75) Inventor: Arthur Kanowitz, Littleton, CO (US)

(73) Assignee: Securisyn Medical, LLC, Littleton, CO (US)

( * ) Notice: Subject to any disclaimer, the term of this patent is extended or adjusted under 35 U.S.C. 154(b) by 116 days.

This patent is subject to a terminal disclaimer.

(21) Appl. No.: 13/080,933

(22) Filed: Apr. 6, 2011

(65) Prior Publication Data

US 2011/0284008 A1 Nov. 24, 2011

Related U.S. Application Data

(63) Continuation-in-part of application No. 11/346,686, filed on Feb. 3, 2006, now Pat. No. 8,001,969.

(60) Provisional application No. 60/593,702, filed on Feb. 7, 2005.

(51) Int. Cl.
*A61M 16/00* (2006.01)
*A62B 9/06* (2006.01)

(52) U.S. Cl.
USPC ............................ 128/207.14; 128/207.17

(58) Field of Classification Search
USPC .............. 128/207.14, 200.26, 207.15–18
See application file for complete search history.

(56) References Cited

U.S. PATENT DOCUMENTS

| | | | | |
|---|---|---|---|---|
| 3,602,227 A * | 8/1971 | Andrew | 128/207.17 |
| 3,760,811 A * | 9/1973 | Andrew | 128/207.17 |
| 4,235,229 A * | 11/1980 | Ranford et al. | 128/207.17 |
| 4,269,184 A * | 5/1981 | Montgomery | 128/207.14 |
| 4,832,019 A * | 5/1989 | Weinstein et al. | 128/207.17 |
| 4,953,548 A * | 9/1990 | Stoddard et al. | 128/207.14 |
| 5,009,227 A * | 4/1991 | Nieuwstad | 128/207.17 |
| 5,069,206 A * | 12/1991 | Crosbie | 128/207.17 |
| 5,320,097 A * | 6/1994 | Clemens et al. | 128/207.17 |
| 5,353,787 A * | 10/1994 | Price | 128/200.26 |
| 8,001,969 B2 * | 8/2011 | Kanowitz | 128/207.14 |
| 2002/0069880 A1* | 6/2002 | Lin | 128/207.15 |
| 2002/0092526 A1* | 7/2002 | Bertoch et al. | 128/207.17 |
| 2006/0082156 A1* | 4/2006 | Runyan | 285/420 |

* cited by examiner

*Primary Examiner* — Justine Yu
*Assistant Examiner* — Colin W Stuart
(74) *Attorney, Agent, or Firm* — Husch Blackwell LLP

(57) ABSTRACT

An airway stabilization system is provided for maintaining an airway device in a patient's trachea and for preventing clinically significant movement thereof with respect to the patient's vocal cords in response to the application of multi-directional forces to the airway device. The system includes a retention collar secured to the airway device to define a retention structure, a restraining device adapted to releaseably engage the retention structure and to cooperate therewith to prevent clinically significant movement of the airway device, and means for securing the restraining device to a patient's head.

9 Claims, 18 Drawing Sheets

COMPLETE AIRWAY STABILIZATION SYSTEM

CROSS-REFERENCE TO RELATED APPLICATIONS

This application is a continuation-in part of U.S. patent application Ser. No. 11/346,686 filed on Feb. 3, 2006, which claims priority to U.S. Provisional Application No. 61/593,702, filed Feb. 7, 2005. The entire disclosures of U.S. patent application Ser. No. 11/346,686 and 61/593,702 are incorporated herein by reference.

FIELD OF THE INVENTION

The present invention relates to a new and improved system designed to maintain an airway in the trachea of a patient. Specifically, the present invention relates to a system for maintaining an airway device in a preselected position in a patient's trachea and for preventing clinically significant movement thereof and unplanned extubation of the patient in response to the application of multidirectional forces to the airway device.

BACKGROUND OF THE INVENTION

Endotracheal intubation is a medical procedure used to place an airway device (artificial airway) into a patient's trachea or airway. The use of an airway device is mandated in situations where an individual is unable to sustain the natural breathing function or maintain an open airway on his or her own due to unconsciousness, trauma, disease, drugs or anesthesia. Thus, life-saving mechanical ventilation is provided through the airway device which may be in the form of an endotracheal tube (ETT), laryngeal mask airway (LMA), King Airway, or one of several other commercially available airway devices.

Endotracheal intubation is accomplished by inserting an airway device into the mouth, down through the throat and vocal cords or voice box, and into the trachea or air passageway which then branches into the bronchial tubes that connect with the lungs. Precisely positioning the airway device in this manner prevents these natural passageways from collapsing or occluding, thereby permitting respiration air to flow into and out of the lungs, but also prevents the aspiration of fluids into the lungs which may cause pneumonia and/or other serious medical complications. Because medical emergencies may occur anywhere, emergency medical service personnel (i.e., paramedics) may be called upon to insert airway devices in out-of-hospital emergency settings as well as in hospital settings by emergency department, operating room, and critical care personnel.

It is very important that the airway device be positioned correctly and maintained in the correct position in the trachea. If the device moves out of its proper position in the trachea and into either the right or left main stem bronchial tube, only one lung will be ventilated. The failure to ventilate the other lung can lead to a host of severe pulmonary complications. Moreover, if the airway device moves completely out of the trachea and into the esophagus, the patient will become hypoxic due to the lack of ventilation to the lungs, a condition which typically results in life-threatening brain injury within a matter of only a few minutes.

Even after an airway device has been positioned correctly, subsequent movement of the patient can lead to inadvertent movement of the device, as hereinabove described. An intubated patient may restlessly move about and may also attempt to forcibly remove an airway device, whether conscious or unconscious, particularly if the patient is uncomfortable or having difficulty breathing, which can lead to panic. Such unintentional movement is not uncommon, particularly when the patient is moved from an out-of-hospital setting, such as an accident scene, to an emergency department of a hospital. Further, anytime an intubated patient may be moved, for example, not only from an ambulance to a trauma facility, but also from one hospital to another hospital, from one area of the hospital to another area in the same hospital (imaging, laboratory, operating theater), or from a hospital to an outpatient rehabilitation facility, unintentional movement of an airway device is a risk. Even repositioning an intubated patient in a hospital bed may cause unintentional movement of the endotracheal tube.

Inadvertent movement of an airway device may also occur as a result of moving external ventilation equipment, such as a conventional mechanical ventilator or bag valve mask, connected thereto where the patient can no longer naturally achieve respiration. Typically, the external ventilation equipment is connected to the external end of the device by an air conduit to establish air flow to and from the lungs. Inadvertent pulling on, or other excessive movement of the air conduit, may transfer movement to the airway device, thereby shifting it from its proper position and causing unplanned extubation.

Unplanned extubation is a hazardous and costly problem which studies have demonstrated occurs at an unacceptably high rate. A study completed by Carson et al reports that approximately 950,000 patients are mechanically ventilated in the United States annually. Carson et al., *The Changing Epidemiology of Mechanical Ventilation: A Population-Based Study. Journal of Intensive Care Medicine.* 2006 February; 21(3): pp. 173-182. A review of the world-wide medical literature suggests that the world-wide rate of unplanned extubation averages approximately 7.1%. Applying the world-wide average to the U.S. figure above, an estimated 68,000 patients in the United States alone experience an unplanned extubation each year. Such unplanned extubations are costly, not only for patients who experience increased rates of morbidity and mortality, but also for hospitals, physicians and insurance companies who incur the liability costs associated therewith. Carson's study referenced above estimates that the annual intensive care unit (ICU) bed cost associated with unplanned extubations in the United States alone is approximately $2.6 M, which includes imaging, pharmacy, and laboratory expenses. (Extrapolated from the cost of long-term care according to the U.S. Department of Health and Human Services National Clearinghouse for long-term care information. See also S. K. Epstein, M. L. Nevins & J. Chung, *Effect of Unplanned Extubation on Outcome of Mechanical Ventilation, Am. Journal of Respiratory and Critical Care Medicine,* 161: 1912-1916 (2000) which discusses the increased likelihood of long-term care outcome). Moreover, it is not unknown for jury damage awards in personal injury law suits arising from unplanned extubations to be in excess of $35 M. The high incidence of unplanned extubations and the associated increase in healthcare costs implies that an improved restraining system is sorely needed which has the capacity to resist the application of greater forces which would otherwise result in movement of the airway device.

Various prior art systems have attempted to address the problem of maintaining an airway device in the correct position and preventing unintentional extubation. The most common approach for securing an airway device (typically, an endotracheal tube) is with adhesive tape. Umbilical tape may be used as an alternative. Both present the same challenges. The tape is tied around the patient's neck and then wrapped and tied around the smooth outside surface of the endotracheal tube itself. Arranged in this fashion, the tape is intended to anchor the endotracheal tube to the corner of the patient's mouth and prevent its unintentional movement. While the use of tape in this manner provides some benefit, the restraint available from the tape usually diminishes because the tape becomes covered and saturated with blood, saliva, or other bodily fluids, thereby diminishing the frictional restraint of the tape around the endotracheal tube. Consequently, the endotracheal tube may be readily moved from its preferred position in the patient's trachea, and this form of securing an airway device provides inadequate protection against movement resulting from the application of multidirectional forces such as bending, torsional/rotational or substantial lateral forces to the device. Such forces may exceed fifty (50) pounds in magnitude, and, as shown in the results of two studies of the restraint capabilities of current devices and methods set forth in Tables 1 and 2 below, such devices and methods do not provide sufficient resistance to prevent unplanned extubation.

Restraint Capabilities of Current Devices and Methods

TABLE 1

|  | Median | Min | Max |
| --- | --- | --- | --- |
| Thomas Tube Holder | 12.98 | 2.64 | 22.44 |
| Adhesive Tape | 19.58 | 3.96 | 39.6 |
| Non Adhesive Tape | 7.48 | 2.42 | 27.72 |

Force to Extubate (7 cm movement) in Lbs
Owens, et al. Resuscitation (2009)

TABLE 2

|  | Median | Min | Max |
| --- | --- | --- | --- |
| Adhesive Tape (Lillehei) | 19.5 | 15 | 25 |
| Tube Tamer | 12.9 | 10 | 15 |
| Precision Medical | 8.6 | 7 | 10 |
| Biomedix Endogrip | 10.7 | 6 | 12 |
| Thomas Tube Holder | 37 | 28 | 43 |

Force to Extubate (2 cm movement) in Lbs
Carlson, et al. Annals of Emergency Medicine 2007

U.S. Pat. No. 5,353,787 issued Oct. 11, 1994, to Price discloses an apparatus having an oral airway for providing fluid communication for the passage of gas from a patient's mouth through his or her throat and into the trachea, the oral airway being releaseably attached to an endotracheal tube for use in combination therewith. While Price's apparatus eliminates the smooth surface of the tube and resists longitudinal movement in relation to the oral airway, the system disclosed by Price does not address the above-identified problem of resisting multidirectional forces. Moreover, Price's device cannot prevent clinically significant movement of an airway device in relation to the vocal cords and an unplanned extubation resulting therefrom.

Other attempts to solve the aforementioned problems have employed auxiliary mechanical securing devices to maintain the position of an endotracheal tube in a patient. Many of these auxiliary mechanical devices include some type of faceplate which is attached to the patient's face, usually with one or more straps that extend around the back of the patient's head or neck. The faceplate includes some type of mechanical contact device that grips the smooth surface of the endotracheal tube. Typical mechanical contact devices include thumb screws, clamps, adhesives, locking teeth, and straps. By way of example, U.S. Pat. No. 4,832,019 issued to Weinstein et al. on May 23, 1989, discloses an endotracheal tube holder which includes a hexagonally-shaped gripping jaw that clamps around the tube after it has been inserted into a patient's mouth and a ratchet-type locking arrangement designed to retain the gripping jaw in position around the tube. Weinstein's patent disclosure states specifically that the tube will not be deformed. However, the fundamental mechanics of a hexagonal receptacle applied around a cylindrical tube to stabilize it reveal that the hexagonal structure will not impart force to the tube of sufficient magnitude to prevent longitudinal movement. As shown in FIG. 1, it has been found that if sufficient pressure is applied directly to the tube by the gripping jaw, the tube will deform or even crush, thereby decreasing ventilatory efficiency to the point that airflow to the patient's lungs will be restricted or even cut off, an extremely serious problem. The outer diameter of a standard 7.5 mm I.D. tube having a cross-sectional area of 44 $mm^2$ is shown at 10. The decrease in cross-sectional area due to deformation or crushing is shown at 15 and is approximately 26.2 $mm^2$. This decrease in cross-sectional area of 40% is the equivalent of using a 4.5 mm I.D. tube.

More recently, U.S. Pat. No. 7,568,484 issued on Aug. 4, 2009, and U.S. Pat. No. 7,628,154 issued on Dec. 8, 2009, both to Bierman et al., disclose endotracheal tube securement systems which include straps extending from the corners of a patient's mouth above and below the patient's ears on each side of the patient's head. However, the devices disclosed in the '484 and the '154 patents merely retain the position of the tube in the patient's mouth and cannot prevent movement thereof in various directions, either longitudinally, rotationally or laterally, as hereinabove described. Moreover, these prior art systems provide no protection for the device itself, inasmuch as the tube is inserted directly into the patient's mouth where it may be pinched or, worse yet, crushed and/or punctured by the biting action of the patient.

Specifically, to maintain an effective restraint, attending medical personnel increase the amount of clamping force applied on an airway device. Increasing the amount of clamping force to an effective level may pinch the device to the point where a portion of the inner tube diameter (and hence air passageway) is significantly restricted. Restricting the cross-sectional size of the air passageway decreases the ventilatory efficiency of the tube, thereby decreasing the respiratory airflow. The restriction of the cross-sectional size of the air passageway creates resistance to both inspiratory airflow and expiratory airflow. The resistance to inspiration creates either a decreased volume of airflow at a given pressure or an increased pressure to maintain a given airflow, both of which, in turn, increase the amount of work a patient must perform to simply breathe. Insufficient airflow can lead to hypoxemia, and increased pressure can lead to barotrauma in the lungs. Resistance to expiratory airflow leads to multiple adverse effects within the lungs. Impairing a patient's ventilations may result in serious medical effects, particularly with patients whose functions are already compromised.

In view of the above, it will be apparent to those skilled in the art from this disclosure that a need exists for an improved airway stabilization system which not only protects an airway device from occlusion and crushing, but also maintains the device in its preferred position in a patient's trachea and prevents clinically significant movement thereof with respect to the vocal cords as a result of the application of multidirectional forces thereto. The present invention addresses this need in the art as well as other needs, all of which will become apparent to those skilled in the art from the accompanying disclosure.

SUMMARY OF THE INVENTION

In order to achieve the above-mentioned objective and other objects of the present invention, a complete airway stabilization system is provided which may be fitted to any airway device to maintain an airway in a patient and which prevents clinically significant movement of the airway device with respect to a patient's vocal cords in response to the application of forces in any direction to the device, be they longitudinal, torsional/rotational or bending. Clinically significant movement is defined as longitudinal movement of the airway device in a direction towards the patient's mouth to a point where the tip of the airway device has moved beyond the vocal cords. Typically, such movement is in the range of five (5) to seven (7) centimeters.

Unlike conventional prior art devices which employ a passive airway device, for example, an endotracheal tube and an active stabilizer, the system disclosed herein comprises at least two active components that cooperate integrally with and engage one another to provide unparalleled strength and stability against movement, even when the endotracheal tube becomes slippery from fluids and/or secretions. Moreover, the system of the instant invention provides the above-referenced strength and stability without applying constricting pressure to the airway device itself. The airway device has a continuous sidewall extending between a proximal and a distal end portion thereof which defines a hollow conduit through which the airway is established. A retention collar is secured to the airway device on the exterior of the sidewall between the end portions. (once attached to the ETT the retention collar is referred to herein as the tracheal tube retention structure ("retention structure"). The retention collar extends along a predetermined length of the sidewall at a predetermined fixed position relative to the distal end to locate at least a portion of the retention collar adjacent to the mouth of the patient when the distal end of the airway device is positioned in the trachea to establish the airway. The retention collar includes a plurality of restraints extending circumferentially about the collar. The restraints substantially increase the active surface area forming a tight interlocking fit with cooperating interlocking portions of a restraining device secured to a patient, thereby establishing a 360° barrier against movement which would otherwise result from forces applied to the device as hereinabove described.

A restraining device is secured to the patient and is configured to releaseably engage the retention structure to prevent clinically significant movement of the distal end of the airway device with respect to the vocal cords of the patient in response to various multidirectional loads or forces which may be applied to the airway device during movement of the patient or by the patient himself. The restraining device includes a plurality of annular flanges structured and arranged to interact with the retention structure at multiple points to maintain the airway device in its preferred position and to form a bite block extending circumferentially around the retention structure and extending into the patient's oral cavity to prevent pinching or crushing of the airway device.

These and other objects, features, aspects and advantages of the present invention will become apparent to those skilled in the art from the following detailed description of preferred embodiments taken in connection with the accompanying drawings, which are briefly summarized below, and by reference to the appended claims.

BRIEF DESCRIPTION OF THE DRAWINGS

Referring now to the attached drawings, which form an integral part of the disclosure.

DETAILED DESCRIPTION

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Figure 1:
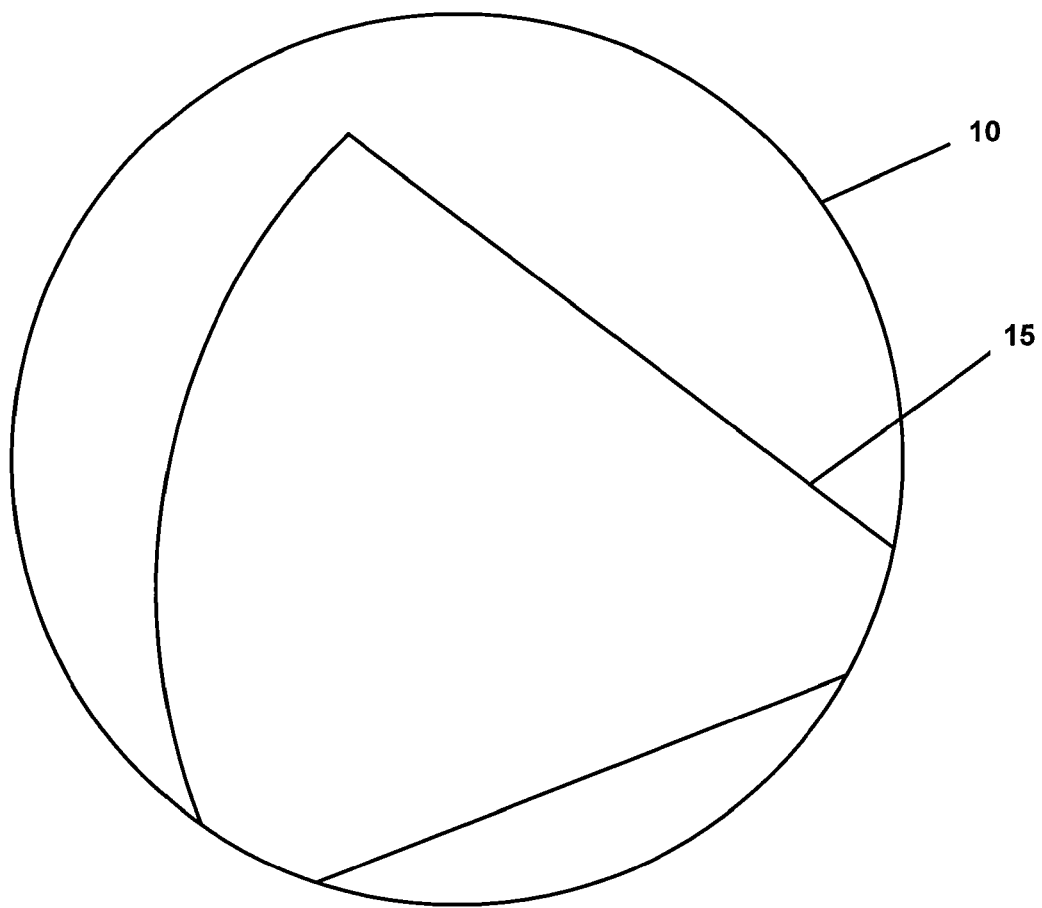
FIG. 1 is a cross-sectional view of an endotrachial tube showing the effects on airflow resulting from tube compression.
Figure 2:
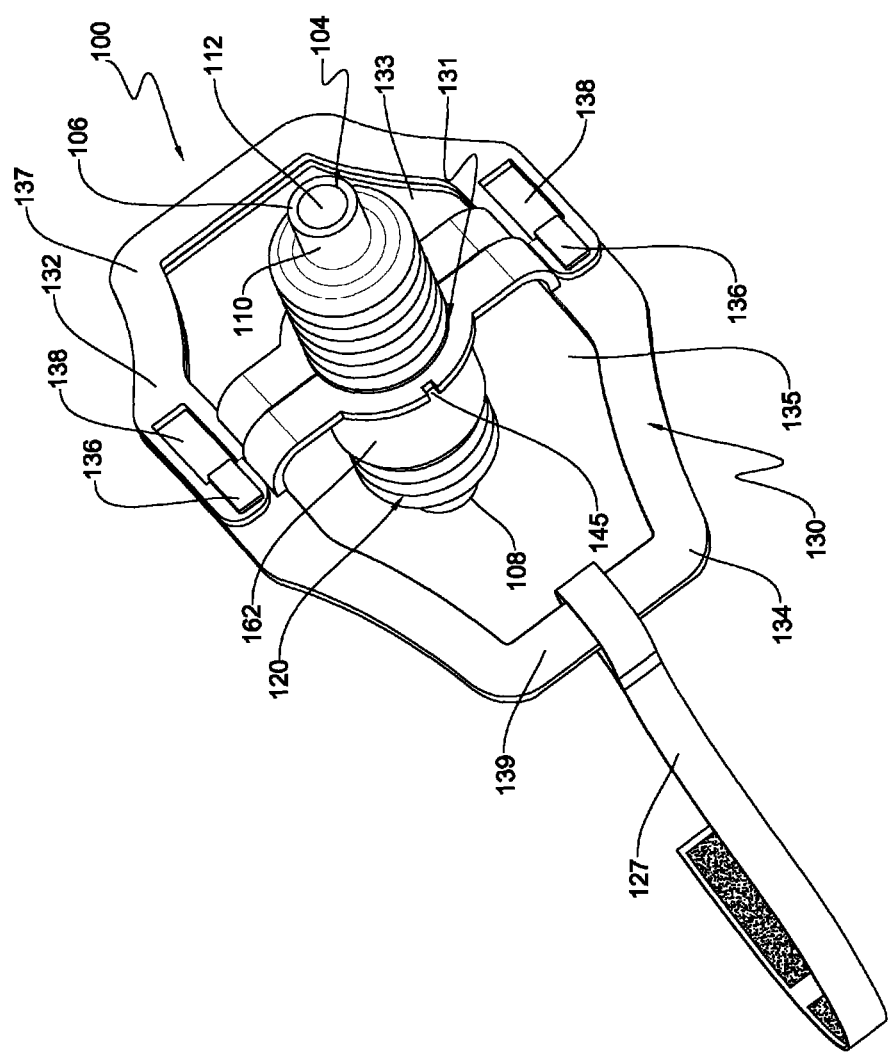
FIG. 2 is a side perspective view of an airway stabilization system of the present invention in accordance with an embodiment.
Figure 14:
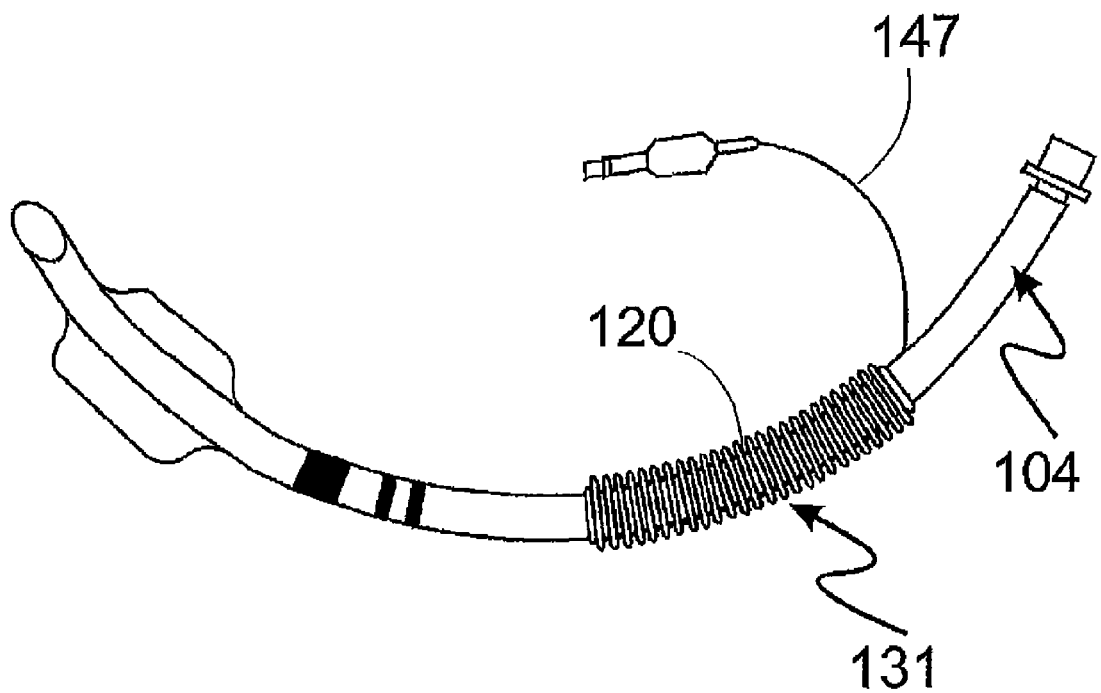
FIG. 14 is a side perspective view of the retention structure of FIG. 2 affixed to an airway device in accordance with an embodiment.
Figure 16:
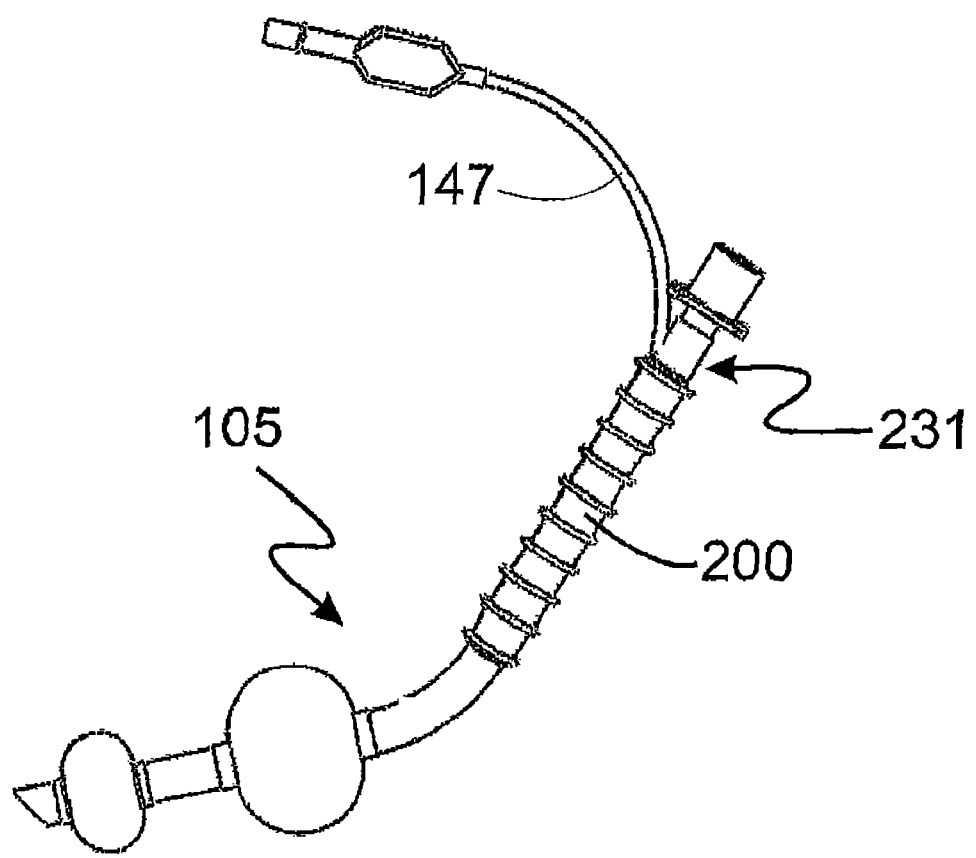
FIG. 16 is a side perspective view of the retention structure of FIG. 3 affixed to a King LT® airway device in accordance with an embodiment.
Figure 17:
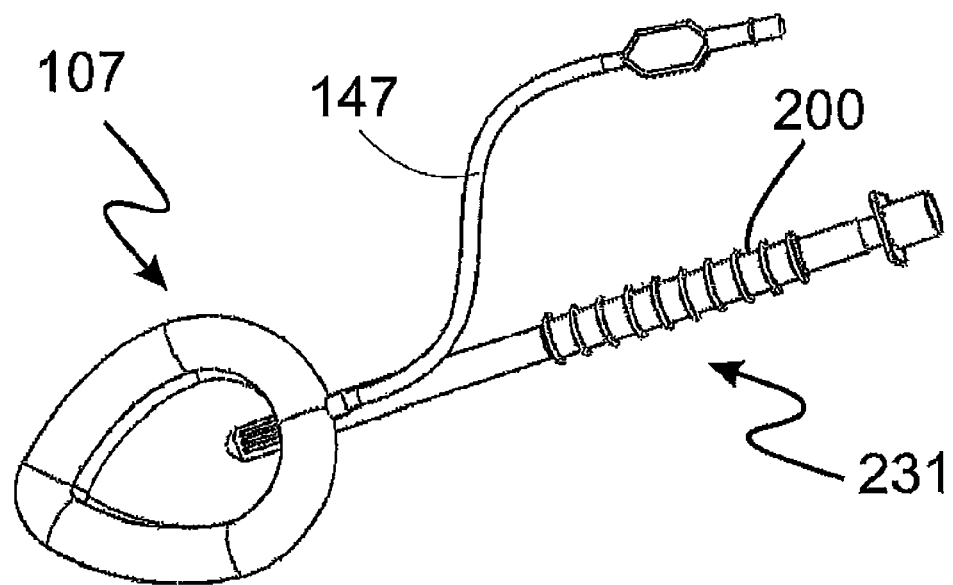
FIG. 17 is a side perspective view of the retention structure of FIG. 3 affixed to a laryngeal mask airway (LMA) airway device in accordance with an embodiment.
Figure 18:
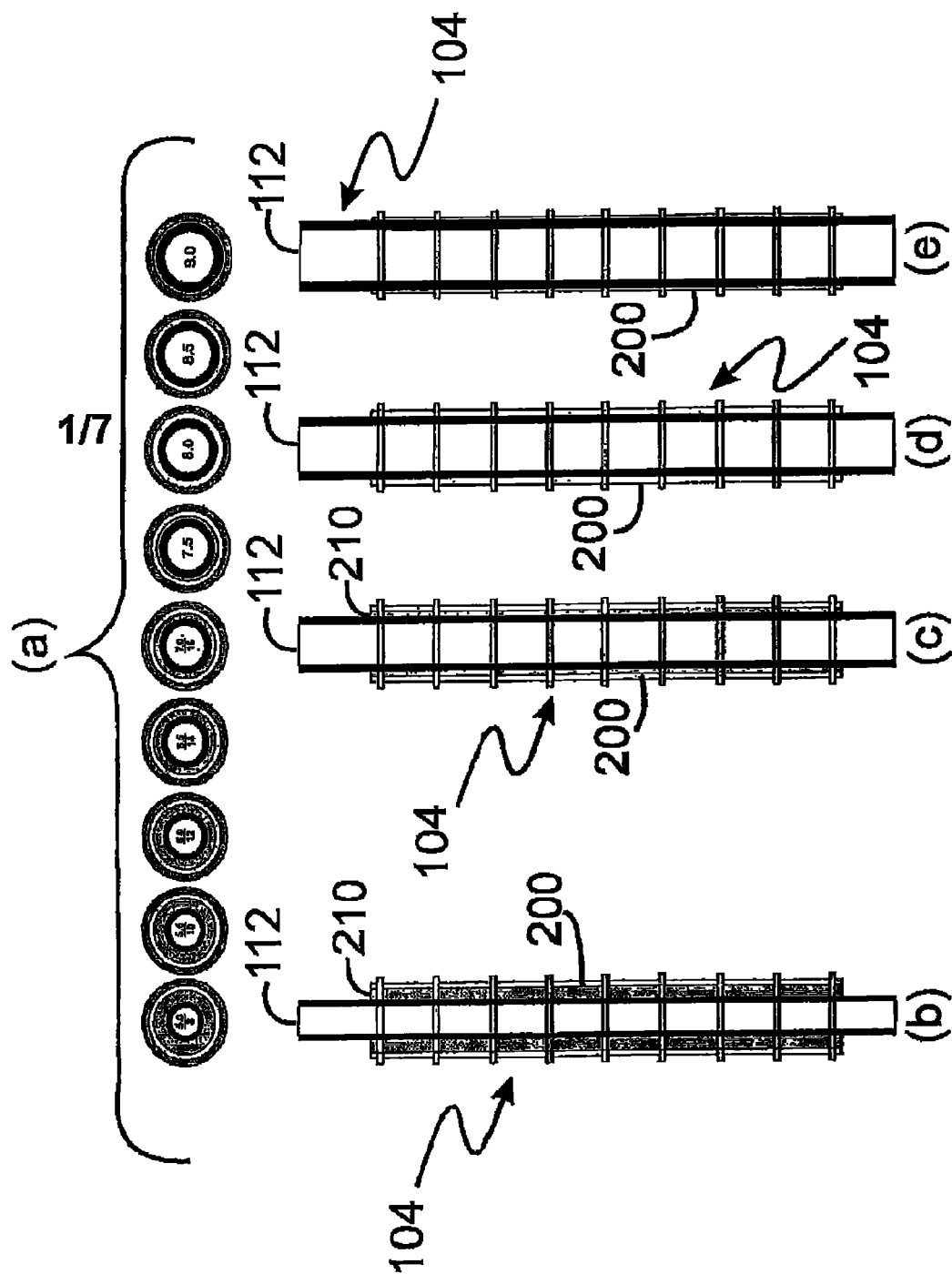
FIG. 18(*a*)-(*e*) are top and side sectional views of the retention collar of the present invention including spacer adapters affixed to airway devices of differing sizes in accordance with an embodiment.

Referring now to FIG. 2, a complete airway stabilization system constructed in accordance with the present invention is shown at 100. The complete airway stabilization system 100 is used to maintain an airway in a patient under conditions where natural respiration is impossible or severely compromised. The airway stabilization system is structured and arranged to cooperate with an airway device shown generally at 104 to establish and maintain an air passageway to a patient's lungs via the patient's mouth, oral cavity, throat, past the patient's vocal cords into the trachea and the bronchial tubes connected thereto for respiration of the patient (not shown). By way of example and not of limitation, the airway device may be in the form of an endotracheal tube as illustrated generally at 104 in FIG. 2 and in greater detail in FIGS. 14 and 15 or one of several other commercially available airway devices such as a King LT® airway device 105 manufactured by King Systems, Noblesville, Ind. shown in FIG. 16, or a laryngeal mask airway (LMA) such as a LMA Classic™ manufactured by LMA North America, San Diego, Calif., as depicted at 107 in FIG. 17. Regardless of its form, the airway device 104 is inserted through the patient's mouth, oral cavity, throat, vocal cords, and into the trachea by using conventional intubation procedures, as is known in the art. The airway stabilization system 100 fits over the patient's face and mouth and interacts with the airway device to maintain its proper position relative to the vocal cords and bronchial tubes for critical ventilation of the patient.

Figure 8:
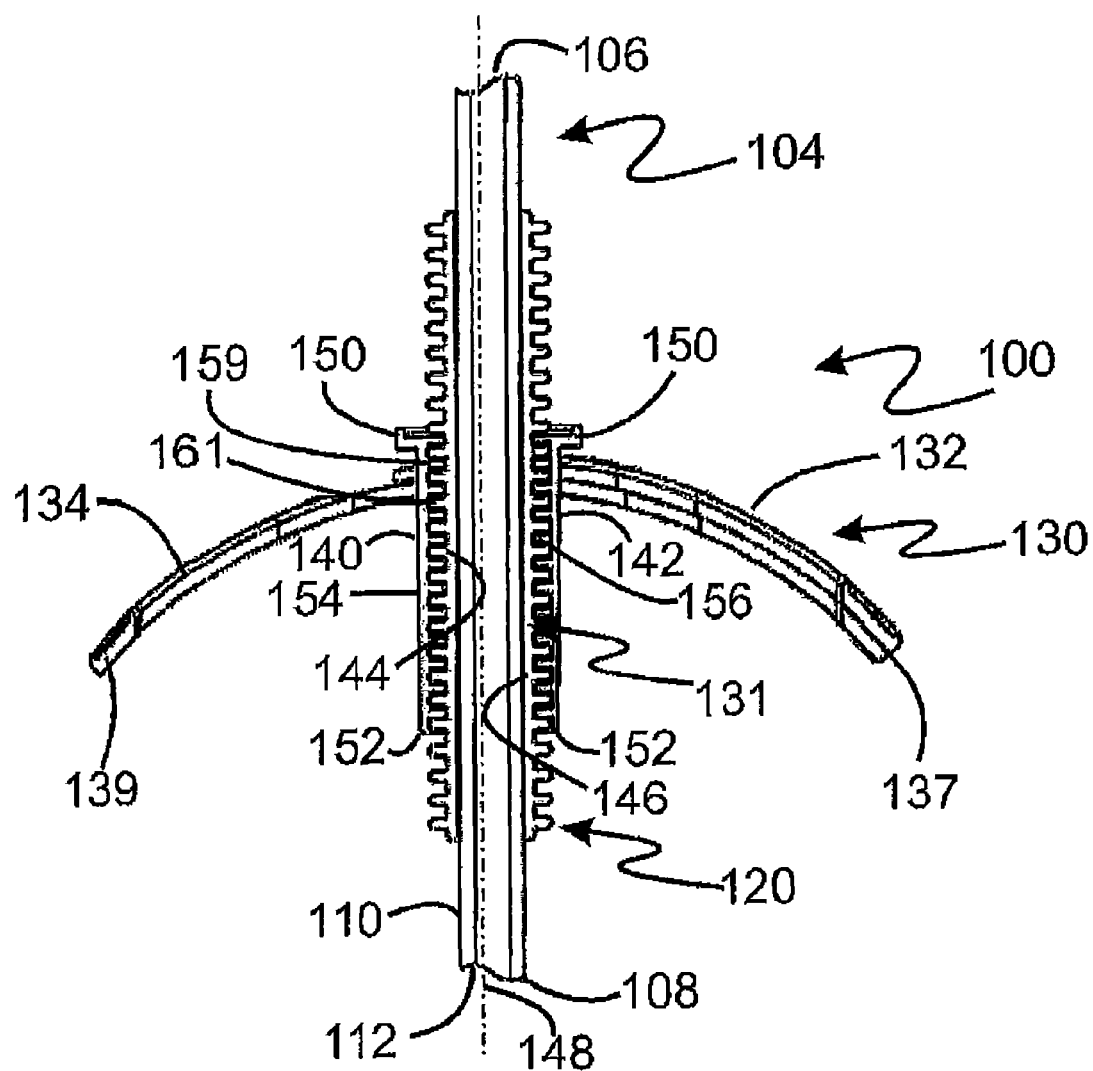
FIG. 8 is a planar cross-sectional view of the airway stabilization system as shown in FIG. 2 having certain portions broken away to more clearly illustrate the details thereof.
Figure 10:
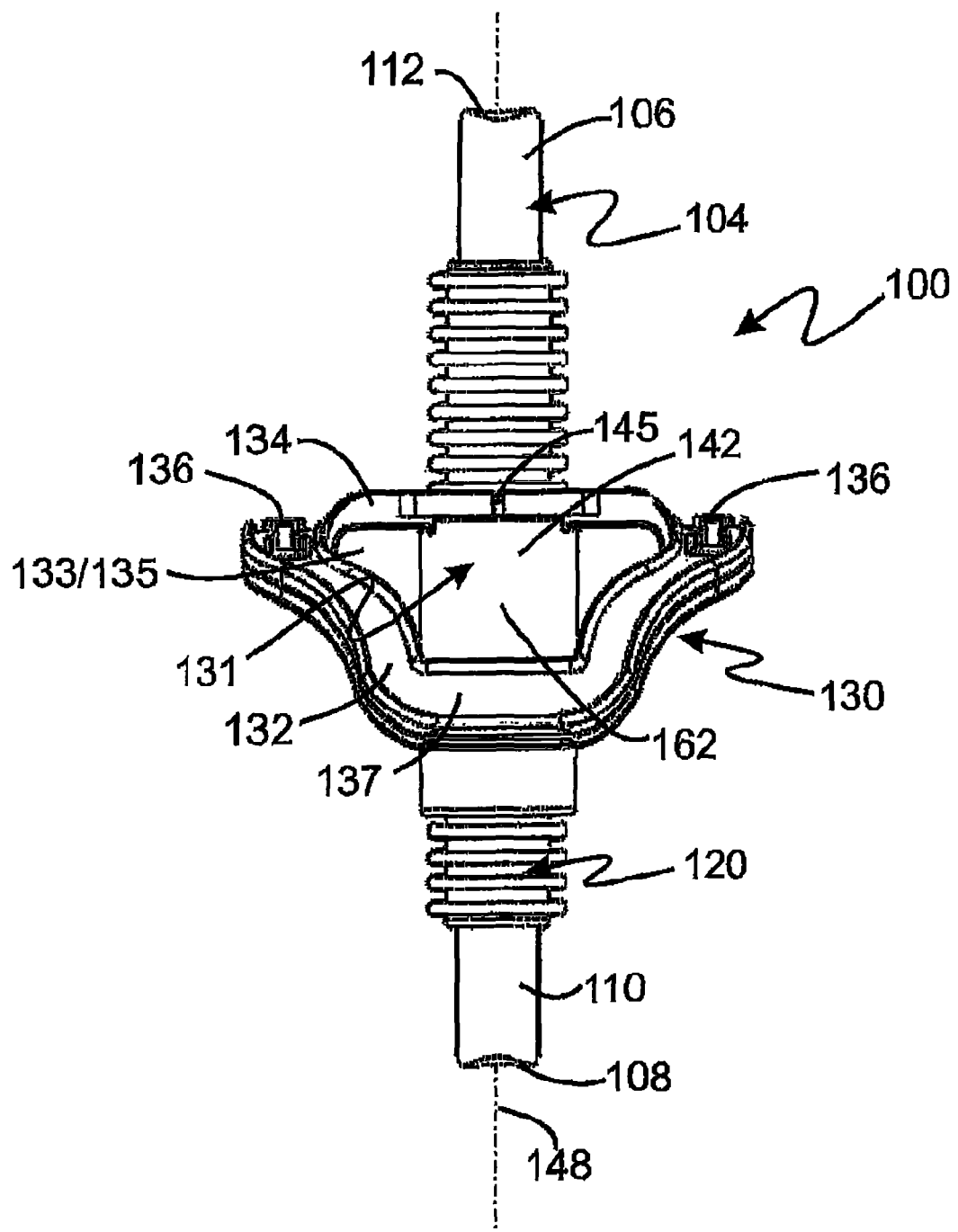
FIG. 10 is a side elevation view of the airway stabilization system of FIG. 2.

Referring to FIGS. 2, 8 and 10, the airway stabilization system 100 includes a retention collar 120 secured to the airway device thereby forming a retention structure 131, a stabilizing device or stabilizer shown generally at 130 adapted to be secured to the patient and structured and arranged to releaseably engage the retention structure 131 and to cooperate therewith to prevent clinically significant movement of the airway device with respect to the patient's vocal cords. As used herein, the term retention structure means a retention collar secured to an airway device. Longitudinal movement of the airway device of approximately 5 to approximately 7 centimeters with respect to the patient's vocal cords as a result of the application of forces in any direction to the device, be they longitudinal, torsional/rotational or bending, is deemed to be clinically significant movement and may result in unplanned and potentially dangerous extubation of the patient. The airway stabilization system further includes means 127 for securing the stabilizing device to the patient. By way of example and not of limitation, the securing means 127 may include straps constructed of rubber, a synthetic material, cloth, plastic or other such materials suitable for the application, which may be affixed to the stabilizer and secured behind the patient's neck or head by clips, buckles, Velcro fasteners and the like. Preferably, to maintain the airway stabilization system in its desired position, the securing means 127 is constructed of a non-stretchable material which prevents significant movement of the stabilizer away from the patient's face.

More specifically, the airway device 104 includes a proximal end portion 106, a distal end portion 108 and a continuous sidewall 110 extending between the proximal and a distal end portion thereof which defines a hollow conduit 112 through which an airway is established. The retention collar 120 is positioned on the exterior of the sidewall 110 between the end portions 106 and 108 and extends along a predetermined length of the sidewall at a predetermined fixed position thereon to locate at least a portion of the retention collar adjacent to the mouth of the patient when the distal end of the airway device is positioned in the trachea to establish the airway. In a preferred embodiment, the retention collar is secured to the airway device by chemical bonding. However, other securing approaches such as adhesive bonding, press fitting or other suitable means may be used to ensure that the retention collar cannot be moved in relation to the airway device without departing from the scope of the instant invention. In an embodiment, the retention collar is integrally molded with the airway device such that the device and the retention structure are, in fact, one piece.

Figure 4:
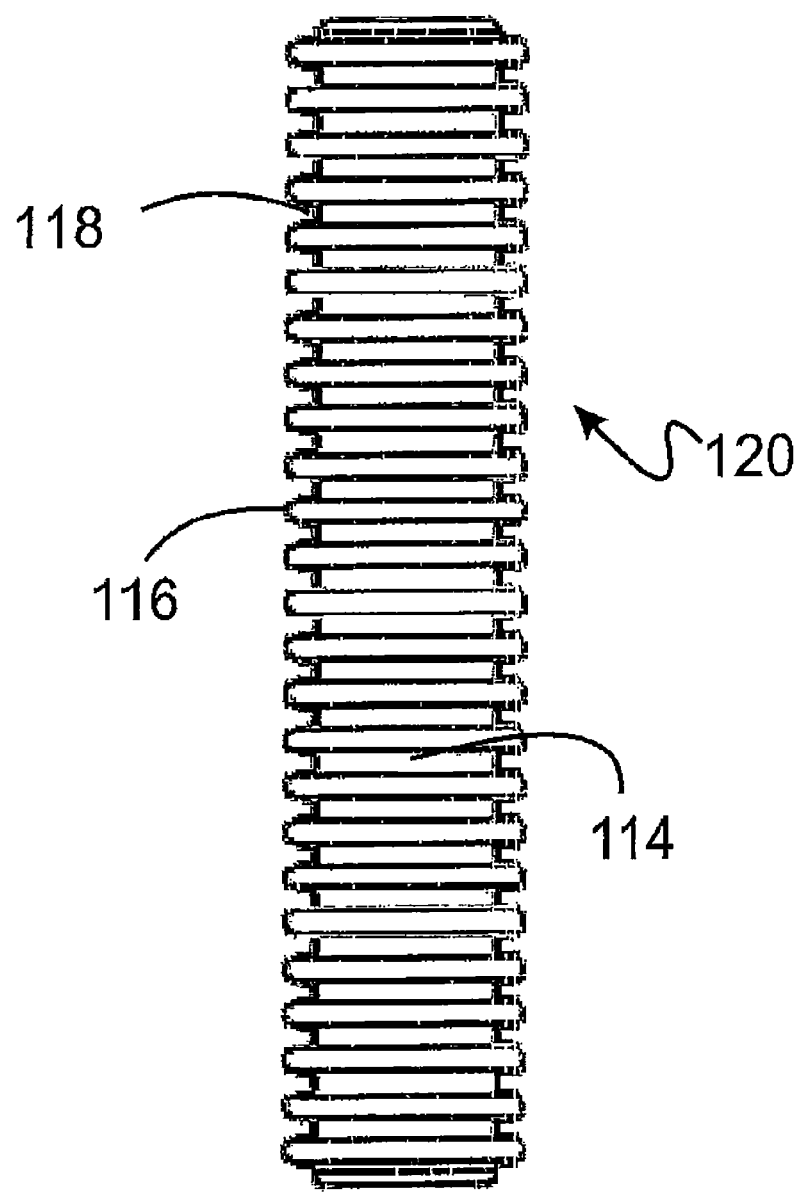
FIG. 4 is a plan view of a retention collar of the airway stabilization system of the present invention system in accordance with an embodiment.
Figure 5:
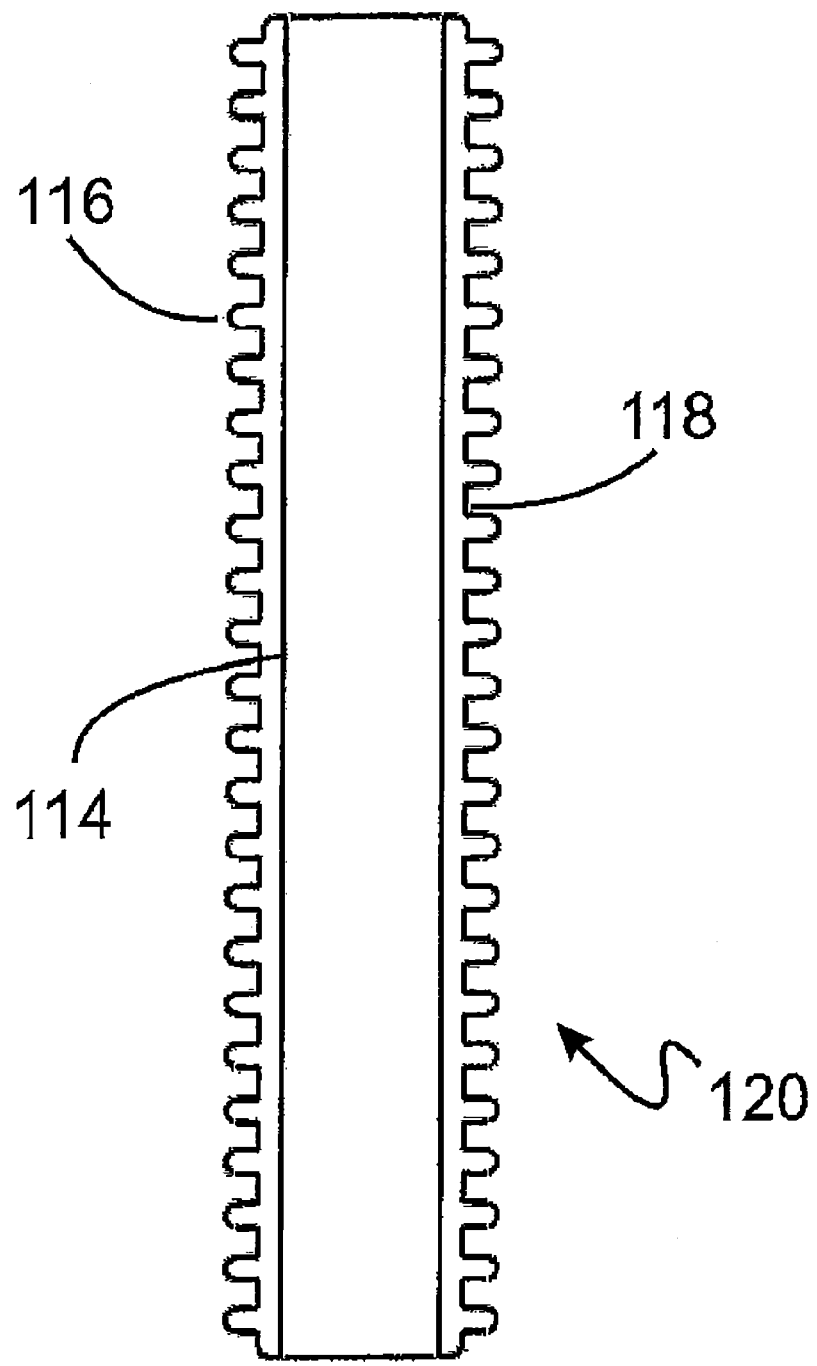
FIG. 5 is a cross-sectional view of the retention collar of FIG. 4.
Figure 6:
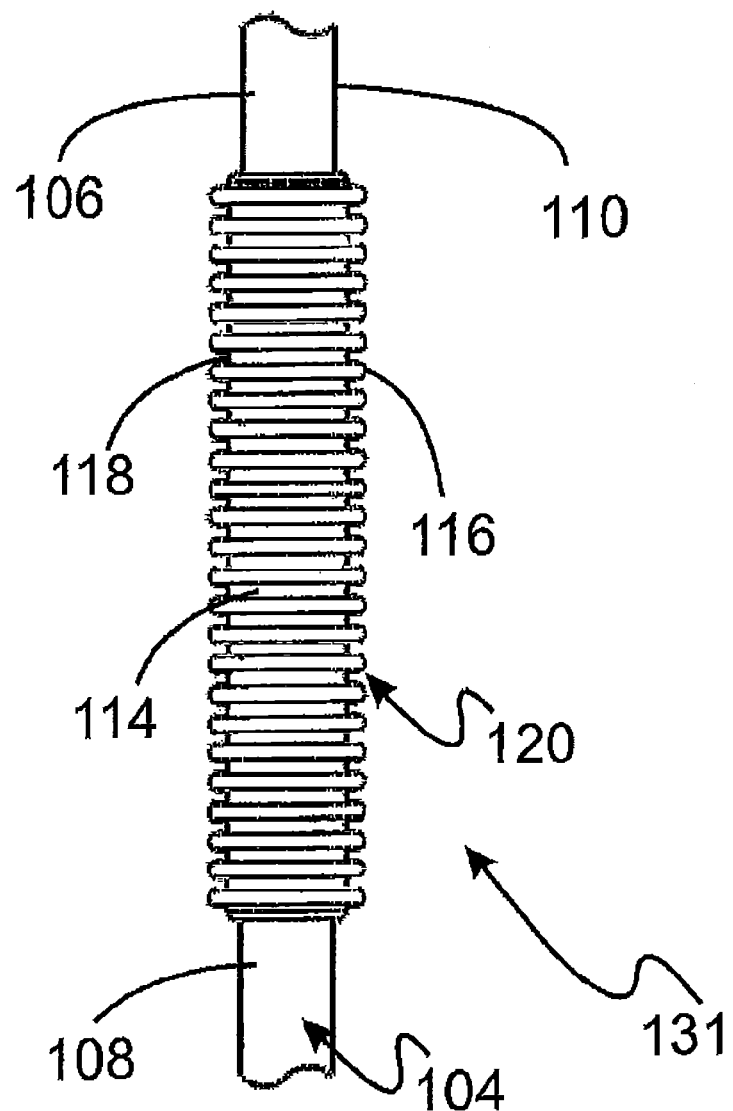
FIG. 6 is an enlarged side plan view of the retention collar of FIGS. 4 and 5 shown in position on an airway device ("retention structure")

Referring to FIGS. 4 and 5, the retention collar 120 is illustrated in greater detail and includes a body portion 114, a plurality of spaced-apart annular flanges or ribs 116 extending substantially radially outwardly from the body portion, each annular flange cooperating with an adjacent annular flange to define a structural recess 118 disposed therebetween. Moreover, as shown in FIG. 6, the increased material thickness of the body portion 114 and the structural recesses serve to reinforce the strength of the entire system and, when positioned over the airway device 104, the retention collar protects the sidewall 110 and conduit 112 against collapse, a much stronger and improved structure over prior art devices which merely incorporate spaced apart annular flanges affixed thereto.

Referring now to FIGS. 8 and 10, the stabilizing device 130 is shown in greater detail and includes a pair of juxtaposed, slidable, overlapping stabilizer sections, more specifically, an upper or top stabilizer section 132 and a lower or bottom stabilizer section 134, each lying in a generally parallel and overlapping plane. Stabilizer sections 132 and 134 may be formed of plastic, rubber, metal, a composite material or other suitable materials having the desired strength and flexion properties suitable for the application. The stabilizer sections are connected together to permit relative movement thereof toward and away from each other. The sliding movement is permitted by a pair of male connectors 136 extending into a pair of correspondingly-located overlapping female channels 138 formed in each of the stabilizer sections 132 and 134. Relative sliding movement of the upper and lower stabilizer sections toward and away from one another is permitted as a result of the male connectors 136 moving along the female channels 138.

Figure 12:
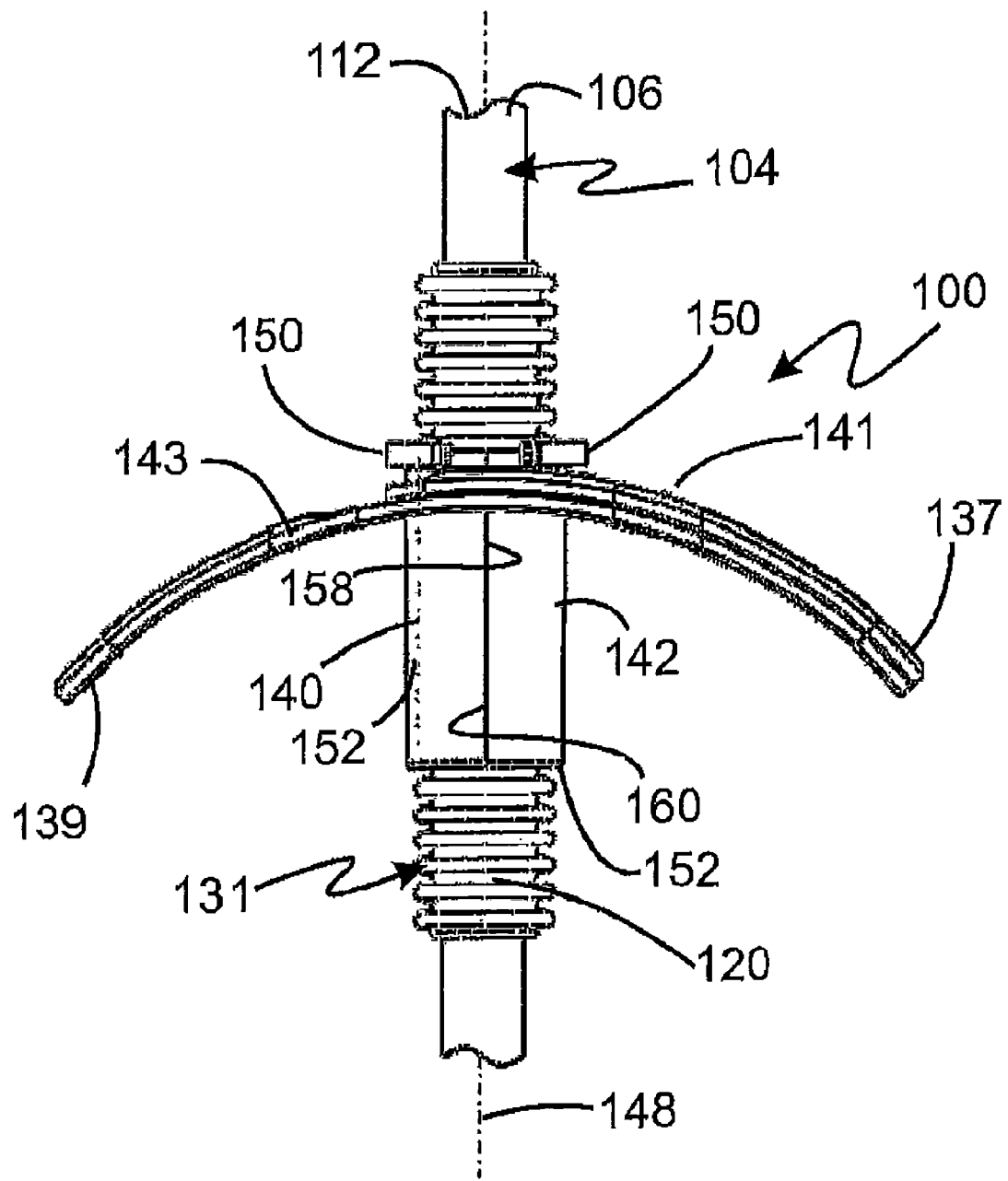
FIG. 12 is a top plan view of the airway stabilization system of FIG. 2.

Each stabilizer section 132 and 134 includes a generally c-shaped section or c-collar 140 and 142 respectively extending in a direction substantially perpendicular to the plane of the stabilizer sections and juxtaposed with respect to one another to releaseably engage the retention collar 120. Each of the c-collars 140 and 142 defines a semi-cylindrically-shaped cavity 144 and 146 respectively about a longitudinal axis 148, each cavity having first and second end portions 150/152, an outer surface 154, an inner surface 156 and a pair of spaced-apart edges 158 and 160 (FIG. 12) disposed between the inner and outer surfaces 154/156 and the first and second end portions 150/152. Each of the edges 158 and 160 extends in a direction substantially parallel to the longitudinal axis 148 and is structured and arranged to releaseably engage the corresponding pair of spaced-apart edges of the collar juxtaposed therewith.

Figure 9:
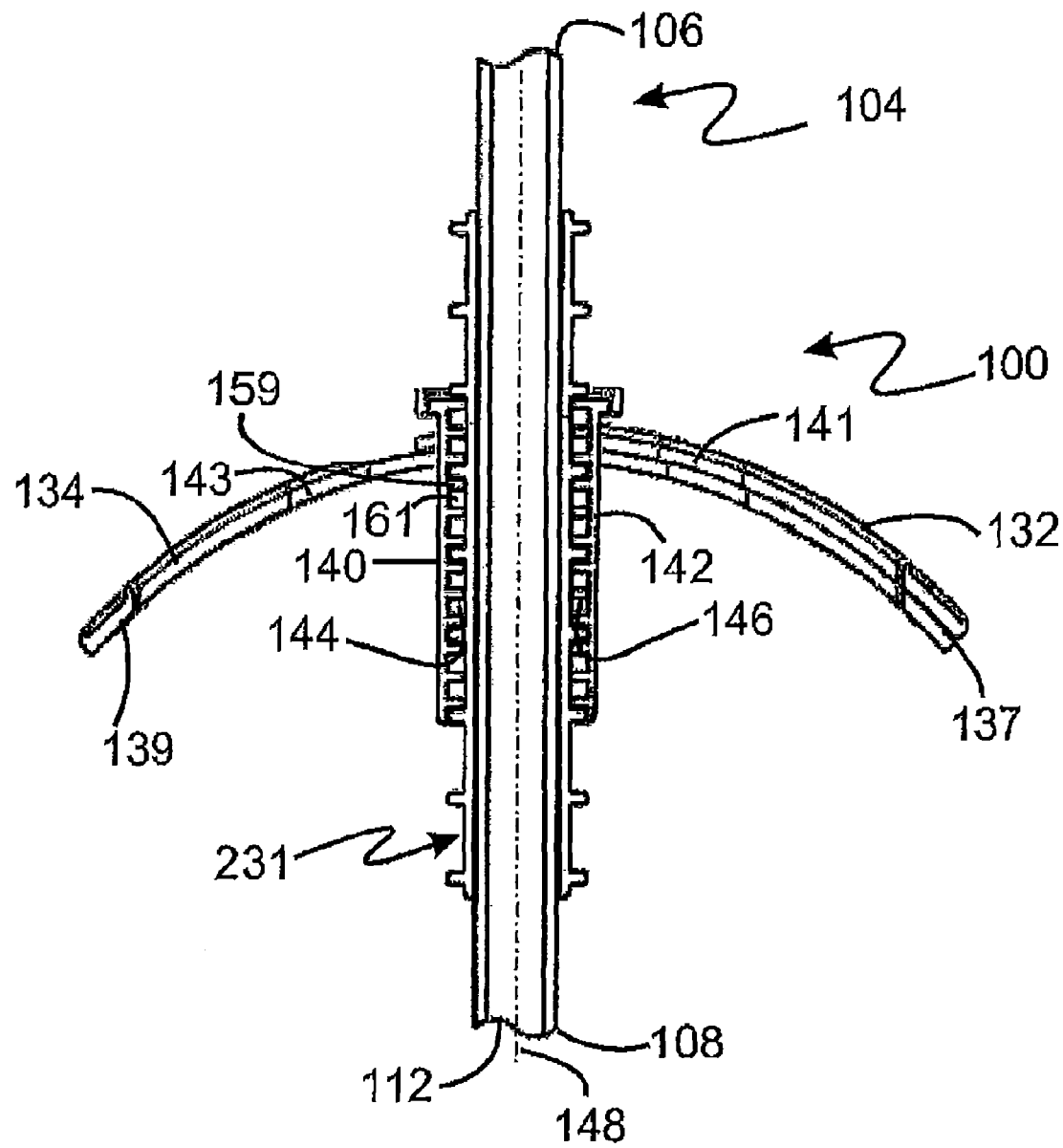
FIG. 9 is a planar cross-sectional view of the airway stabilization system as shown in FIG. 2 having certain portions broken away to more clearly illustrate the details thereof.

Referring now to FIGS. 8 and 9, each of the c-collars 140 and 142 includes a plurality of spaced-apart annular flanges 159 extending substantially radially inwardly from the inner surface thereof, each annular flange cooperating with an adjacent annular flange to define a structural recess 161 disposed therebetween. The inwardly-extending annular flanges and structural recesses of the stabilizer are structured and arranged to releaseably engage corresponding mating structural recesses and outwardly-extending annular flanges of the retention apparatus to interlock with one another when the c-collars are urged into a closed position about the retention apparatus by the securing means, thereby creating multiple points of contact and interaction between the two elements of the stabilization system and thus preventing clinically significant movement of the airway device in response to substantial forces which may be applied thereto in any direction. Moreover, in the closed position, the c-collars form a bite block shown generally at 162 in FIG. 2 which is adapted to be removably inserted into the patient's oral cavity. Unlike prior art systems which clasp the tube of the airway device directly and focus on preventing movement resulting from single direction longitudinal forces, the restraining apparatus of the instant invention completely encapsulates the airway device, not only isolating it totally from any pinching or crushing forces, but also securing it against movement resulting from the application of torsional/rotational, bending and longitudinal forces which may be applied, as well. Moreover, unlike prior art systems, the bite block of the instant invention does not have a smooth inner surface. Rather, the plurality of spaced apart annular flanges 159 and structural recesses 161 actively participate in the stabilization of the overall airway system by providing a multiple level 360 degree interface between the bite block and the retention structure which creates a significant barrier to movement which occurs as a result of the application of multidirectional forces to the airway device.

Referring again to FIG. 2, each of the stabilizers 132 and 134 includes an aperture 133 and 135, respectively for permitting access to the patient's face, mouth and oral cavity for administering medications and hygiene. The laterally-extending members 137 and 139 of each stabilizer 132/134 respectively are bent in a generally downwardly direction for the plane of each to conform to the patient's face, and each further has a plurality of recesses 141 and 143 formed therein to facilitate facial conformance. A notch 145 is also formed in each stabilizer, to receive a tube 147 for inflation of the airway devices of FIGS. 14-17, as necessary. The notch 145 fixes the tube in position such that the tube is maintained against the outer surface 154 of the bite block 162, thus preventing an intubated patient from biting down upon and puncturing the tube.

Figure 3:
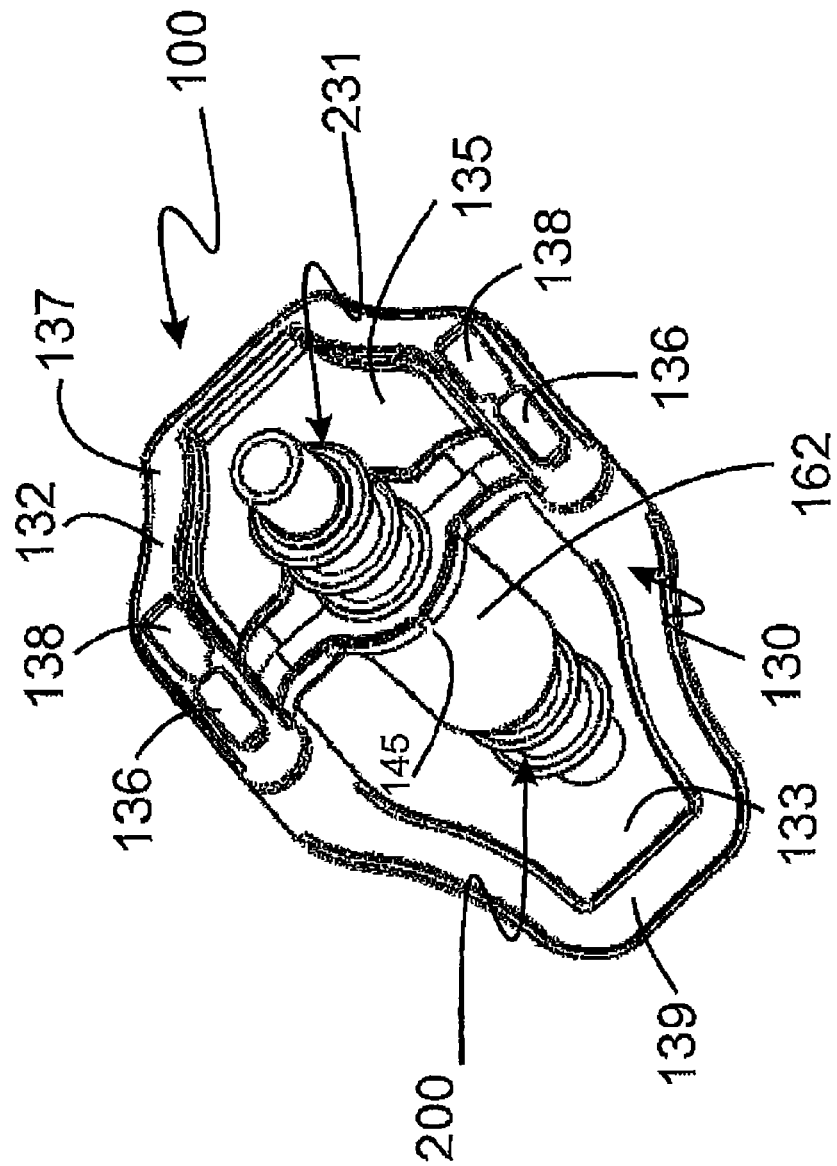
FIG. 3 is a side perspective view of an airway stabilization system of the present invention in accordance with another embodiment.
Figure 11:
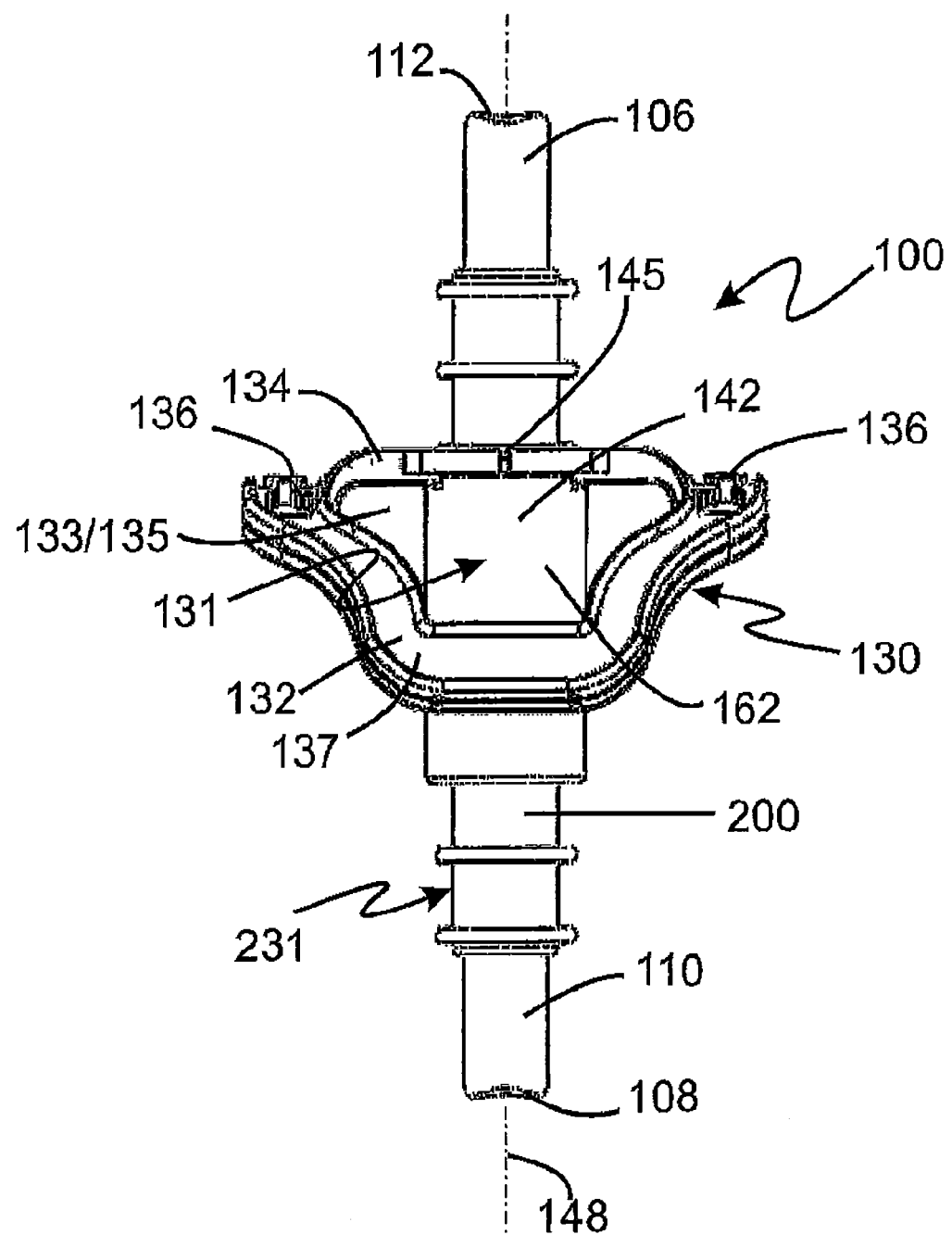
FIG. 11 is a side elevation view of the airway stabilization system of FIG. 3.
Figure 13:
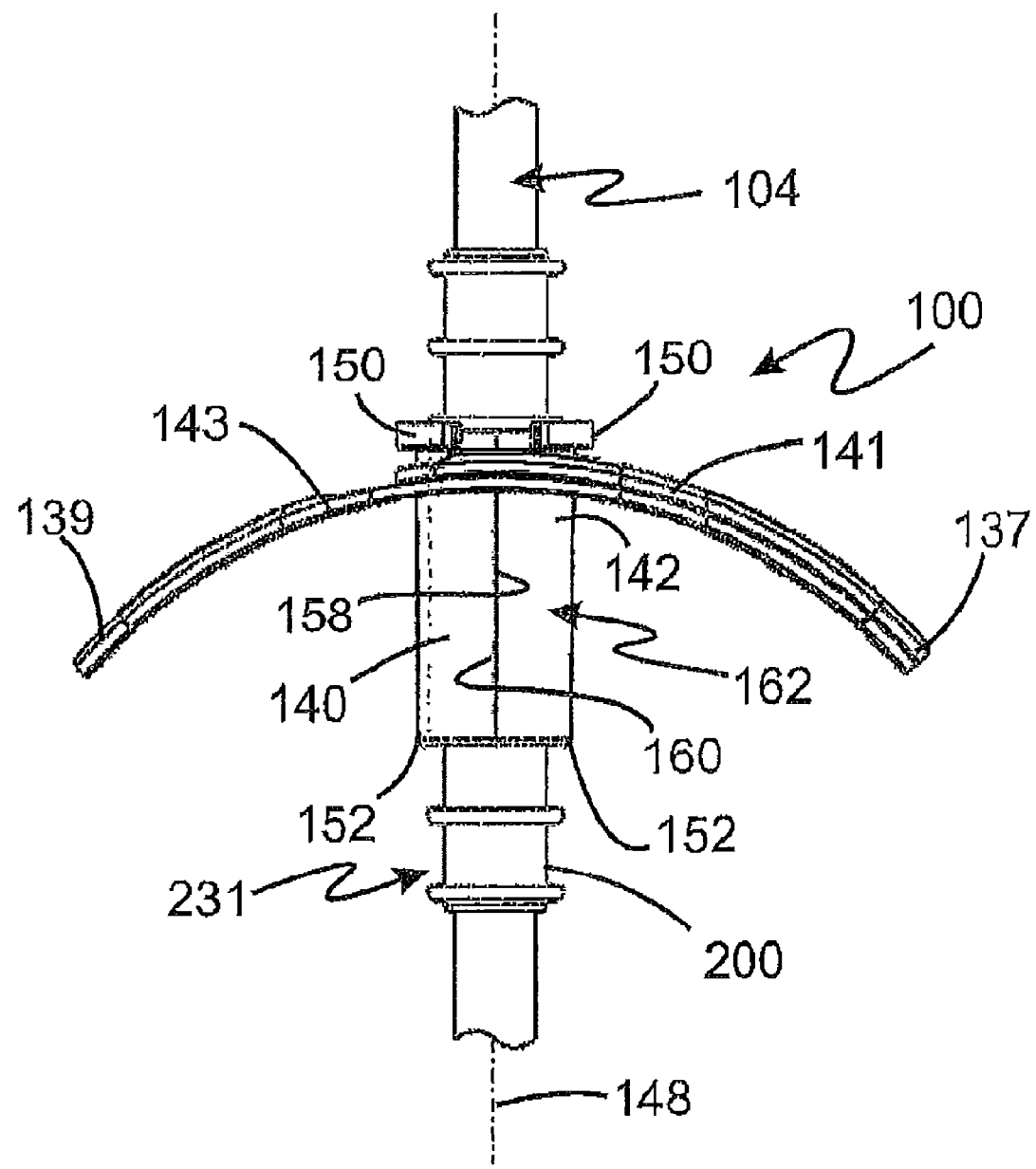
FIG. 13 a top plan view of the airway stabilization system of FIG. 3.

Referring now to FIG. 3, the airway stabilization system 100 of the present invention is shown adapted to releaseably engage a retention collar 200 secured to an airway device 120 to form a retention structure 231 which prevents clinically significant movement of the airway device with respect to the patient's vocal cords as hereinabove described. In application, the retention collar 200 is installed on an airway device 104 in substantially the same fashion as the retention collar 120 of the embodiment of FIG. 2 and is depicted as-installed in greater detail in FIGS. 9, 11 and 13.

Figure 7:
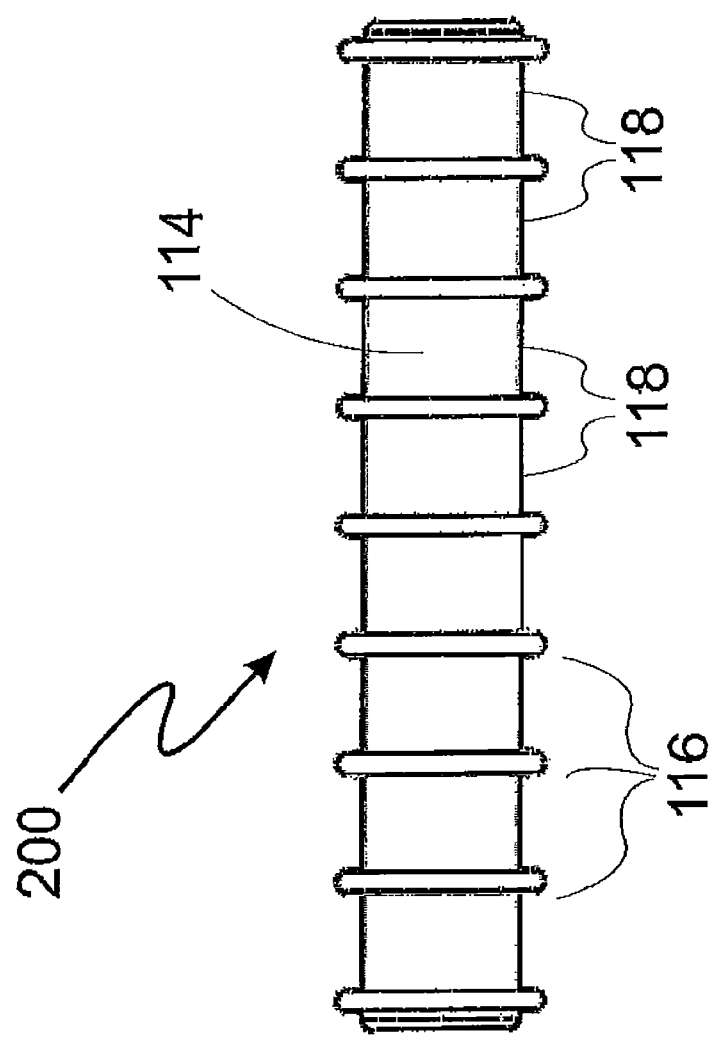
FIG. 7 is a side perspective view of a retention collar in accordance with another embodiment.
Figure 15:
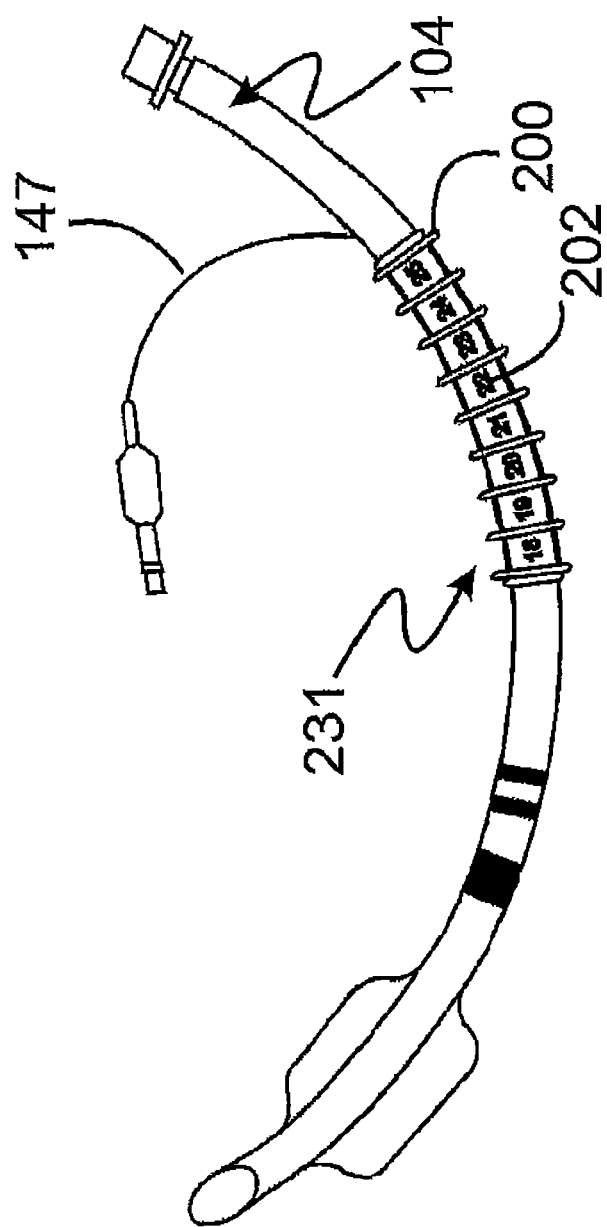
FIG. 15 is a side perspective view of the retention structure of FIG. 3 affixed to an airway device in accordance with an embodiment.

As illustrated in greater detail in FIG. 7, the retention collar 200 is of substantially the same construction, configuration and function as the retention collar 120 of the embodiment of FIG. 4 and includes a body portion 114, a plurality of spaced-apart annular flanges or ribs 116 extending substantially radially outwardly from the body portion, each annular flange cooperating with an adjacent annular flange to define a structural recess 118 disposed therebetween. The ribs 116 of retention collar 200 are spaced approximately one (1) centimeter apart to permit marking of the retention collar with distance indicators 202 as shown in FIG. 15. The distance indicators are marked strategically on the retention collar at the ½ centimeter positions, and the retention collar is positioned precisely on the airway device with respect to the distal end 108 so that the distance indicators provide personnel performing an intubation with an accurate indication of the insertion depth of the airway device in a patient's trachea.

In practice, commercially available airway devices have hollow conduits 112 of varying diameters which establish the airway in an intubated patient. FIGS. 18(a)-(e) illustrate exemplary airway devices having internal diameters ranging in size from approximately 5 mm to approximately 9 mm; although, airway devices of other sizes are also available. For purposes of manufacturing economy and marketing and distribution practicality, it is desirable to produce an airway stabilization system which may be advantageously used in conjunction with airway devices of varying dimensions without the need for providing retention collars and/or upper and lower stabilizer sections of varying sizes. Accordingly, spacers 210 of suitable dimension may be inserted in the retention collar 200, the spacers being structured and arranged to be secured to both the airway device and to the retention collar as hereinabove described so as to prevent clinically significant movement of an airway device of any size with respect to the patient's vocal cords. Due to manufacturing process and related tolerances, larger core pins may be used to adjust the wall thicknesses and accompanying interior diameters of the retention collars. Accordingly, the use of a spacer may not be needed with retention collars designed for 8.0 mm and 8.5 mm airway device tubes (FIG. 18(c)). However, due to potential constraints on the retention collar wall thickness, all tubes requiring a retention collar having an interior diameter of less than 7.5 mm may utilize a spacer to fill in the gap between the interior wall of the retention collar and the exterior wall of the tube.

Many other advantages and improvements will be apparent upon gaining a full understanding and appreciation of the various aspects of the complete airway stabilization system. Presently preferred embodiments of the invention and many of its improvements have been described with a degree of particularity. This description is a preferred example of implementing the invention, and is not necessarily intended to limit the scope of the invention.

What is claimed is:

1. An airway stabilization system for maintaining an airway device in a patient's trachea, the patient having a head, a face, a mouth, an oral cavity, vocal cords, a neck, a chest and a chin, the system comprising:

a retention structure secured to the airway device;

a restraining device adapted to be secured to the patient, the restraining device being structured and arranged to releaseably engage the retention structure and to cooperate therewith to prevent clinically significant movement of the airway device with respect to the patient's vocal cords in response to application of multidirectional forces to the airway device, the restraining device including a pair of slidable overlapping stabilizer sections, each stabilizer section being operatively connected to one another and adapted to be positioned over the mouth of the patient, each stabilizer section including a collar extending distally therefrom along the airway device substantially the same distance as the collar on the other stabilizer section, the collars being juxtaposed with respect to one another to form a bite block about the retention structure with both collars, the collars being structured and arranged to releaseably engage the retention structure and to provide a multiple level 360 degree interface between the restraining device and the retention structure, the retention structure completely encapsulating the airway device, whereby the airway device is isolated totally from any pinching or crushing forces; and at least one fixation band operatively connected to the restraining device;

wherein the retention structure includes a body portion and a plurality of spaced-apart annular flanges extending radially outwardly from the body portion, wherein the retention structure further includes a plurality of structural recesses disposed between adjacent outwardly-extending flanges, wherein each of the collars includes a plurality of spaced-apart annular flanges extending substantially inwardly from an inner surface thereof, wherein each of the collars further includes a plurality of structural recesses disposed between adjacent inwardly-extending annular flanges, wherein the outwardly-extending annular flanges and structural recesses of the retention structure are structured and arranged to releaseably engage the inwardly-extending flanges and adjacent structural recesses of each of the collars to prevent clinically significant movement of the airway device in response to the application of forces thereto in any direction.

2. The airway stabilization system of claim 1 wherein each of the collars defines semi-cylindrically shaped cavity about a longitudinal axis, each cavity having first and second end portions, an outer surface, an inner surface and a pair of spaced-apart edges disposed between the inner and outer surfaces and the first and second end portions, the edges of each collar extending in a direction substantially parallel to the longitudinal axis and being structured and arranged to engage the corresponding pair of spaced-apart edges of the other collar.

3. The airway stabilization system of claim 1 wherein the restraining device is structured and arranged to releaseably engage the retention structure, respective adjacent annular flanges of the restraining device and the retention structure creating multiple points of contact and interaction therebetween to prevent clinically significant movement of the airway device in response to the application of forces thereto in any direction.

4. The airway stabilization system of claim 1 wherein the airway device has an outer circumference and wherein a circumference of the inwardly-extending annular flanges of each of the collars is approximately equal to the outer circumference of the airway device.

5. The airway stabilization system of claim 1 wherein the airway device is an endotracheal tube.

6. The airway stabilization system of claim 1 wherein the airway device is a supraglottic airway device.

7. The airway stabilization system of claim 1 wherein each of the overlapping stabilizer sections is contoured to adapt to the patient's face.

8. The airway stabilization system of claim 7, wherein each of the overlapping stabilizer sections is contoured to curve distally over the collars.

9. The airway stabilization system of claim 1 wherein each of the overlapping stabilizer sections has an aperture formed therein to permit access to the patient's oral cavity.

* * * * *